ent Number: 5,039,805
Date of Patent: Aug. 13, 1991

United States Patent [19]
Alig et al.

[54] NOVEL BENZOIC AND PHENYLACETIC ACID DERIVATIVES

[75] Inventors: Leo Alig, Kaiseraugst; Albrecht Edenhofer, Riehen; Marcel Müller, Frenkendorf, all of Switzerland; Arnold Trzeciak, Schopfheim, Fed. Rep. of Germany; Thomas Weller, Basel, Switzerland

[73] Assignee: Hoffmann-La Roche Inc., Nutley, N.J.

[21] Appl. No.: 440,949

[22] Filed: Nov. 24, 1989

[30]  Foreign Application Priority Data

Dec. 8, 1988 [CH]  Switzerland ..................... 4543/88
Oct. 11, 1989 [CH]  Switzerland ..................... 3703/89

[51] Int. Cl.$^5$ ............... C07D 211/56; C07D 211/92; C07C 229/20; C07C 229/04
[52] U.S. Cl. .................... 546/224; 546/225; 546/233; 546/234; 560/13; 560/21; 560/22; 560/34; 560/38; 560/39; 560/41; 562/430; 562/435; 562/437; 562/439; 562/444; 562/449; 562/450
[58] Field of Search ............... 546/224, 225, 233, 234

[56]  References Cited
U.S. PATENT DOCUMENTS
4,578,079  3/1986  Ruoslahti et al. ................. 546/224

FOREIGN PATENT DOCUMENTS
0220957  5/1987  European Pat. Off. .

Primary Examiner—Johann Richter
Attorney, Agent, or Firm—George M. Gould; Willliam H. Epstein; Bruce A. Pokras

[57]  ABSTRACT

The compound of the formula

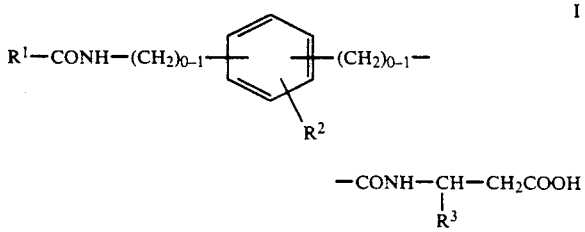

wherein $R^1$, $R^2$ and $R^3$ have the significance given in the description, can be used as medicaments for the therapy and prophylaxis of disorders such as thromboses, stroke, cardiac infarct, inflammations and arteriosclerosis as well as for the treatment of tumours.

3 Claims, No Drawings

NOVEL BENZOIC AND PHENYLACETIC ACID DERIVATIVES

SUMMARY OF THE INVENTION

The present invention relates to novel benzoic acid and phenylacetic acid derivatives, a process for their manufacture, pharmaceutical preparations which contain such compounds as well as the use of these compounds in the manufacture of pharmaceutical preparations.

DETAILED DESCRIPTION

In particular, the invention is concerned with benzoic acid and phenylacetic acid derivatives of the formula

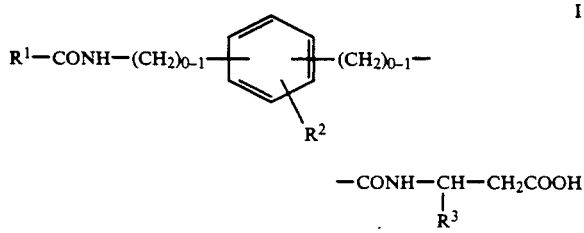

wherein
R$^1$ is a group of the formula

   (R-1)

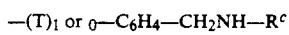   (R-2)

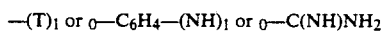   (R-3)

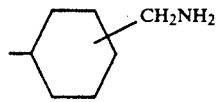   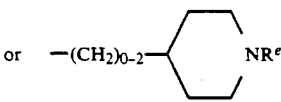

(R-4)                (R-5)

R$^a$ is H, NH$_2$, —NHCOO—C$_{1-4}$-alkyl, —NH—Z or —NHCOCH$_2$N(Y)—CH$_2$CH$_2$NH—Y and n is 1–6 or, where
R$^a$ is H, n can also be 0,
Y is H, Boc or Z;
R$^b$ is H, amidino or —C(NH)—(CH$_2$)$_{0-3}$—CH$_3$;
R$^c$ is H or amidino;
T is —CH$_2$—, —CH=CH— or —C(H,R$^d$)—CH$_2$—;
R$^d$ has the same significance as R$^a$ or is —NHCO—phenyl, —NHCO—phenylene—N$_3$ or —NHSO$_2$—aryl;
R$^e$ is H or amidino;
R$^3$ is H, —CONH$_2$, —COR$^f$, —COOR$^g$ or aryl;
R$^f$ is the residue of an α-aminocarboxylic acid attached via the amino group or of an ester or amide thereof;
R$^g$ is H or lower-alkyl;
R$^2$ is H, CH$_3$, OCH$_3$, NO$_2$, halogen, NH$_2$, —NHCO—phenylene—COOH, —NHCO(CH$_2$)$_{1-4}$—COOH, OR$^h$, —CH$_2$CH$_2$OR$^h$, —CH$_2$CH$_2$OCH$_2$CH$_2$OR$^h$ or —CH$_2$COOR$^h$; and
R$^h$ is H or lower-alkyl,
as well as hydrates or solvates and physiologically usable salts thereof.

In the scope of the present invention Me denotes methyl, Bzl denotes benzyl, tBu denotes t-butyl, Boc denotes t-butoxycarbonyl, Z denotes benzyloxycarbonyl, Arg denotes L-arginyl, Orn denotes L-ornithyl, Val denotes L-valyl, Phe denotes L-phenylalanyl, Leu denotes L-leucyl, Ileu denotes L-isoleucyl, Ser denotes L-seryl, Thr denotes L-threonyl, Gly denotes glycyl, Ala denotes L-alanyl and Asp denotes L-α-aspartyl.

Aryl denotes mono- or bicyclic residues such as phenyl, tolyl and α- or β-naphthyl.

Examples of α-aminocarboxylic acids attached via the amino group are Val, Phe, Leu, Ileu, Ser, Thr, N-isopropyl-Gly, β-cyclohexyl-Ala, β-(1-naphthyl)-Ala and cycloleucine.

The compounds of formula I can be solvated, especially hydrated. The hydration can be effected in the course of the manufacturing process or can occur gradually as a consequence of hygroscopic properties of an initially anhydrous compound of formula I.

Examples of physiologically usable salts of the compounds of formula I are salts with physiologically compatible mineral acids such as hydrochloric acid, sulphuric acid or phosphoric acid or with organic acids such as methanesulphonic acid, acetic acid, trifluoroacetic acid, citric acid, fumaric acid, succinic acid or salicylic acid. The compounds of formula I can also form salts with physiologically compatible bases. Examples of such salts are alkali metal, alkaline earth metal, ammonium and alkylammonium salts such as the Na, K, Ca or trimethylammonium salt. Compounds of formula I which contain an amino, amidino or guanidino group can be present in the form of zwitterions.

The compounds of formula I which contain one or more asymmetric C atoms can be present as enantiomers, as diastereomers or as mixtures thereof, e.g. as racemates.

A preferred group of compounds of formula I comprises compounds of the formula

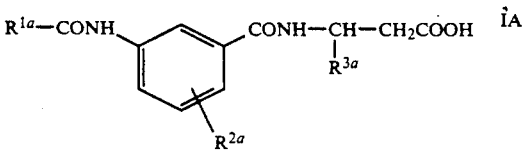

wherein
R$^{1a}$ is a group of formula R-1, R-2 or R-3;
R$^{2a}$ is H, —CH$_3$, —OCH$_3$, —NO$_2$, halogen, —NH$_2$, —NHCO—phenylene—COOH or —NHCO(CH$_2$)$_{1-4}$—COOH;
R$^{3a}$ is H, —CONH$_2$ or —COR$^i$;
R$^i$ is the residue of an α-aminocarboxylic acid attached via the amino group
and R-1, R-2 and R-3 have the significance given above.

Preferred compounds of formulae I and IA are, further, those in which R$^1$ represents an (amino or guanidino)—(CH$_2$)$_{1-7}$—, α-(amino or guanidino)-(m or p)-tolyl or α-amino-p-tolylmethyl group or in which R$^1$—CO— represents the acid residue of arginine, ornithine or N$^2$-Boc-ornithine or represents 3-(p-amidinophenyl)-DL-alanyl or p-amidinobenzoyl.

Further, there are preferred the compounds of formulae I and IA in which R$^3$ is hydrogen, carboxyisobutylideneaminocarbonyl or 1-carboxy-2-(1-naphthyl)-ethylideneaminocarbonyl as well as those in which R$^2$ is H, CH$_3$, OCH$_3$, NO$_2$ or Cl.

The compounds of formula I can be obtained in accordance with the invention by cleaving off ester group(s) and/or amino, amidino or guanidino protecting group(s) from a compound of the formula

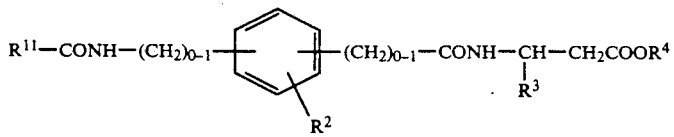

wherein $R^{11}$ represents a residue of formula R-1, R-2, R-3, R-4 or R-5 defined above in which an optionally present amino, amidino or guanidino group can be present in protected form, $R^4$ is hydrogen or a readily cleavable ester group and $R^2$ and $R^3$ have the significance given above; and whereby the molecule contains at least one readily cleavable ester group or a protected amino, amidino or guanidino group, if desired, functionally modifying a reactive group present in the residue $R^1$ and, if desired, converting a compound of formula I into a physiologically usable salt or converting a salt of a compound of formula I into the free acid or base.

Examples of protected amino, amidino and guanidino protecting groups are —NH—Z, —NH—Boc and azido; —C(NH)NH—Z; —NHC(NH)NH—NO₂ and —NHC(N—Boc)—NH—Boc. Methyl, t-butyl and benzyl are examples of readily cleavable ester groups $R^4$. Benzyloxycarbonylisobutylideneamino is an example of a residue $R^f$ which is present in the form of a readily cleavable ester.

The cleavages of the ester groups and of the NH₂-protecting groups can be carried out in a manner known per se. For example, an ester group can be saponified with a base such as an alkali metal hydroxide, e.g. sodium hydroxide solution. Benzyl esters can be cleaved by hydrogenation in the presence of a noble metal catalyst such as palladium-on-carbon (Pd/C) in a solvent such as methanol, ethanol, formic acid or acetic acid at a temperature up to about 40° C., preferably at room temperature. Amino or amidino protecting groups such as Z or guanidino protecting groups such as NO₂ present in the group R are thereby simultaneously cleaved off.

A protected amino group, e.g. —NH—Boc, present in the substituent $R^{11}$ can be cleaved e.g. with an acid such as formic acid or trifluoroacetic acid at a temperature up to 40° C., preferably at about room temperature. Thereby, ester groups $R^4$, e.g. t-butyl, are simultaneously cleaved or amidino protecting groups such Boc are simultaneously cleaved off.

The functional modifications of reactive groups in $R^1$ can also be carried out according to customary methods. Thus, a primary amino group —NH—$R^b$ or —NH—$R^c$ present in the substituent $R^1$ can be transformed into a guanidino group, e.g. using 2-[(aminoiminomethyl)thio]ethanesulphonic acid in the presence of a base such as sodium carbonate or sodium hydroxide at a temperature up to 40° C., preferably at about room temperature.

A primary amino group $R^a$ present in a substituent $R^1$ can be transformed into the —NH—Boc group, e.g. using di-t-butyl dicarbonate in a solvent such as dioxan in the presence of pyridine hydrobromide and sodium bicarbonate at a temperature up to 40° C., preferably at about room temperature.

Conversely, a protected amino group $R^a$ such as —NH—Boc present in the substituent $R^1$ can be cleaved off, e.g. using formic acid as described above in connection with the cleavage of protecting groups.

The compounds of formula II are novel and are also an object of the present invention. Their preparation can be effected starting from known compounds according to methods which are known per se and which are familiar to any person skilled in the art.

Thus, compounds of formula II can be obtained by coupling an acid of the formula $$R^{12}—COOH \qquad III$$

with an amine of the formula

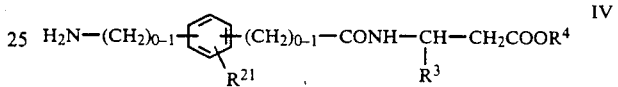

or coupling an acid of the formula

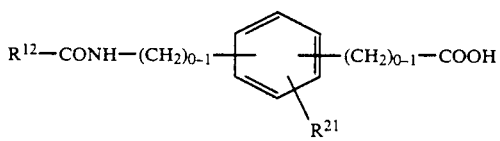

with an amine of the formula $$H_2N—CH(R^3)—CH_2COOR^4 \qquad VI$$

wherein $R^3$ and $R^4$ have the above significance and $R^{12}$ and $R^{21}$ represent a residue $R^1$ and $R^2$, respectively, in which an optionally present amino, amidino or guanidino group can be present in protected form. with the formation of an amide bond. If desired, ester groups and amino, amidino or guanidino protecting groups present in the thus-obtained reaction product can then be cleaved off selectively. The coupling reactions of the acids of formulae III and V with the amines of formulae IV and VI, respectively, can be carried out according to methods which are known per se from peptide chemistry.

An acid of formula III can be activated e.g. with isobutyl chloroformate and triethylamine in tetrahydrofuran (THF) at a temperature between about −10° C. and room temperature and reacted with the trifluoroacetate of a base of formula IV at the stated temperature.

An acid of formula V can be activated e.g. in THF with 2-chloro-4,6-dimethoxy-1,3,5-triazine and N-methylmorpholine and reacted with the p-toluenesulphonate of an amine of formula VI. The acid V can also be activated in dimethylformamide (DMF) with isobutyl chloroformate and N-methylmorpholine and reacted with the trifluoroacetate of the amine VI at a temperature between about −5° C. and room temperature.

An ester group, e.g. methoxycarbonyl, present in an ester of formula II can be cleaved selectively, e.g. by saponification in methanolic sodium hydroxide solution. An amino protecting group such as Boc present in the ester II thereby remains.

Protected amidino groups, which can be present as precursors of the residues R-1, R-2 and R-3, can be prepared from corresponding nitriles by reaction with hydrogen sulphide and triethylamine in pyridine to give the thioamide, methylation with methyl iodide and subsequent reacted with ammonium acetate in methanol. The protecting group can then be introduced by treating the amidine with benzyl chloroformate and triethylamine in THF. A protected guanidino group can be synthesized from an amino group by reaction with N,N'-bis(tert-butoxycarbonyl)-S-methyl-isothiourea in tert.butanol in the presence of triethylamine.

The amines of formula IV can be prepared in a manner known per se starting from an acid of the formula

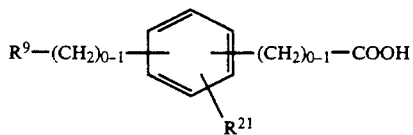

VII wherein $R^9$ is a protected amino group such as —NH—Boc. and an amine of formula VI: and the acids of formula V can be prepared starting from an acid of formula III and a compound of the formula

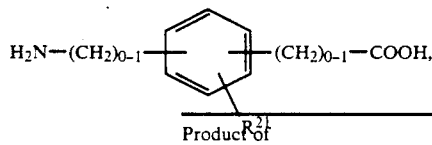

VIII whereby the procedure described above for the reaction of the compounds III and V can be used. Amines of formula IV can also be prepared by reacting an acid of formula VII with an amine of the formula $$H_2NCH(COOCH_3)CH_2COOR^4$$ IX to a give a compound of the formula

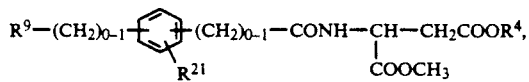

X saponifying the —COOCH₃ group and reacting the acid obtained with an amine HR/.

Furthermore, numerous Examples which follow contain detailed information concerning the preparation of specific compounds of formula II. The starting materials of formulae III, VI, VIII, VIII-1, IX and XII are known, e.g. from J. Med. Chem. 13 (1970) 352; Nippon Kagaku Zasshi 78 (1957) 1768 or DOS 3 700 166, or can be prepared according to methods which are known per se and which are familiar to a person skilled in the art.

The compounds of formula I, their solvates and their salts inhibit not only the binding of fibrinogen, fibronectin and the Willebrand factor to the fibrinogen receptor of blood platelets (glycoprotein IIb/IIIa), but also the binding of these and further adhesive proteins such as vitronectin, collagen and laminin to the corresponding receptors on the surface of different types of cell. The said compounds therefore influence cell-cell and cell-matrix interactions. In particular, they prevent the formation of blood platelet thrombi and can be used in the control or prevention of illnesses such as thrombosis, stroke, cardiac infarct, inflammation and arteriosclerosis. Further, these compounds have an effect on tumour cells in that they inhibit their metastasis. Accordingly, they can also be used as antitumour agents.

The inhibition of the binding of fibrinogen to the fibrinogen receptor, glycoprotein IIb/IIIa, can be demonstrated as follows:

The glycoprotein IIb/IIIa is obtained from Triton X-100 extracts of human blood platelets and is purified by lectin affinity chromatography (Analytical Biochemistry 151, 1985, 169–177) and chromatography on an Arg-Gly-Asp-Ser affinity column (Science 231, 1986, 1559–62). The thus-obtained receptor protein is bonded to microtitre plates. The specific binding of fibrinogen to the immobilized receptor is determined with the aid of an ELISA system ("enzyme-linked immunosorbent assay"). The $IC_{50}$ values hereinafter correspond to that concentration of the test substance which is required to inhibit the binding of fibrinogen to the immobilized receptor by 50%:

| Product of Example: | 5 | 8 | 9 | 10 | 13 | 14 | 15 | 17 | 21 | 22 | 24 | 28 | 32 | 34 | 35 |
|---|---|---|---|---|---|---|---|---|---|---|---|---|---|---|---|
| $IC_{50}$ (μM) | 0.27 | 0.16 | 0.24 | 0.26 | 0.22 | 0.3 | 0.08 | 0.38 | 0.46 | 0.25 | 0.38 | 0.14 | 0.12 | 0.046 | 0.0001 |
| Product of Example: | 36 | 41 | 46 | 47 | 51 | 52 | 53 | 54 | 55 | 56 | 60 | 64 | 65 | | |
| $IC_{50}$ (μM) | 0.27 | 0.28 | 0.15 | 0.18 | 0.017 | 0.14 | 0.07 | 0.01 | 0.025 | 0.005 | 0.05 | 0.22 | 0.084 | | |

The compounds of formula I are non-toxic. Thus, the product of Example 10 has a $LD_{50}$ of more than 1000 mg/kg intraperitoneally and more than 2000 mg/kg perorally in the mouse.

As mentioned earlier, medicaments containing a compound of formula I, a solvate thereof or a salt thereof are likewise an object of the present invention, as is a process for the manufacture of such medicaments which comprises bringing one or more of the said compounds and, if desired, one or more other therapeutically valuable substances into a galenical administration form. The medicaments can be administered enterally, e.g. orally in the form of tablets, coated tablets, dragees, hard and soft gelatine capsules, solutions, emulsions or suspensions, or rectally, e.g. in the form of suppositories, or as a spray. The administration can, however, also be effected parenterally, e.g. in the form of injection solutions.

The active ingredient can be mixed with pharmaceutically inert, inorganic or organic excipients for the manufacture of tablets, coated tablets, dragees and hard gelatine capsules, Lactose, maize starch or derivatives thereof, talc, stearic acid or its salts can be used e.g. as such excipients for tablets, dragees and hard gelatine capsules. Vegetable oils, waxes, fats, semi-solid and liquid polyols are suitable e.g. as excipients for soft gelatine capsules; depending on the nature of the active ingredient no excipients are, however, generally required in the case of soft gelatine capsules. For the manufacture of solutions and syrups there are suitable as excipients e.g. water, polyols, saccharose, invert sugar and glucose, for injection solutions there are suitable e.g. water, alcohols, polyols, glycerine and vegetable oils, and for suppositories there are suitable e.g. natural or hardened oils, waxes, fats and semi-liquid or liquid polyols. Moreover, the pharmaceutical preparations can contain preserving agents, solubilizing agents, stabilizing agents, wetting agents, emulsifying agents, sweetening agents, colouring agents, flavouring agents, salts for varying the osmotic pressure, buffers, coating agents or antioxidants.

For the control or prevention of the illnesses mentioned above, the dosage of the active ingredient can vary within wide limits and will, of course, be adjusted to individual requirements in each particular case. In general, in the case of oral administration a dosage of about 0.1 to 20 mg/kg, preferably of about 0.5 to 4 mg/kg, per day should be appropriate for adults, although the upper limit just given can also be exceeded when this is shown to be indicated.

EXAMPLE 1

900 mg of N-[m-[[N$_2$-[(benzyloxy)carbonyl]-N$_5$-(N-nitroamidino)-L-ornithyl]amino]benzoyl]-$\beta$-alanine benzyl ester and 300 mg of Pd/C (5%) are stirred in 20 ml of formic acid for 18 hours under hydrogen. The reaction mixture is filtered and the filtrate is evaporated in a vacuum. The residue is taken up in water and again evaporated in a vacuum. After drying there are obtained 545 mg of N-[m-(L-arginylamino)benzoyl]-$\beta$-alanine formate (2:3), $[\alpha]_D^{20} = +39°$ (H$_2$O, c=0.5%).

For the preparation of the ester starting material, m-(1-t-butoxyformamido)benzoic acid in THF is activated (2 hours, 0° C.) with 2-chloro-4,6-dimethoxy-1,3,5-triazine and N-methylmorpholine and reacted with $\beta$-alanine benzyl ester p-toluenesulphonate and N-methylmorpholine to give N-[m-(1-t-butoxyformamido)benzoyl]-$\beta$-alanine benzyl ester, m.p. 130°-131° C. Cleavage with trifluoroacetic acid gives N-(m-aminobenzoyl)-$\beta$-alanine benzyl ester trifluoroacetate. N$_\alpha$-Z-N$_\omega$-Nitro-L-arginine is activated (4 minutes, −10° C.) with isobutyl chloroformate and triethylamine in THF and coupled with N-(m-aminobenzoyl)-$\beta$-alanine benzyl ester trifluoroacetate and triethylamine to give the desired benzyl ester, m.p. 157°-160° C.

EXAMPLE 2

N-[m-(L-Arginylamino)benzoyl]-$\beta$-alanine formate is adsorbed in water on Amberlite IR-120 (H$^+$), a strongly acidic cation exchange resin containing SO$_3$H groups, and washed neutral with deionized water. Free N-[m-(L-arginylamino)benzoyl]-$\beta$-alanine, m.p. 93°-95° C., is subsequently eluted with aqueous ammonia (2%).

EXAMPLE 3

390 mg of N-[3-[[N$_2$-(benzyloxycarbonyl)-N$_5$-(N-nitroamidino)-L-ornithyl]amino]-p-anisoyl]-$\beta$-alanine benzyl ester and 160 mg of Pd/C (5%) are stirred in 8 ml of formic acid for 5 hours under hydrogen. The filtered solution is evaporated and the residue is purified on silica gel with methanol-formic acid (99:1). There are obtained 195 mg of N-[3-(L-arginylamino)-p-anisoyl]-$\beta$-alanine formate (1:2), $[\alpha]_D^{20} = +46.6°$ (H$_2$O, c=0.5%).

For the preparation of the ester starting material, N$_\alpha$-Z-N$_\omega$-nitro-L-arginine in THF is activated with 2-chloro-4,6-dimethoxy-1,3,5-triazine and N-methylmorpholine and reacted with 3-amino-4-methoxybenzoic acid and N-methylmorpholine to give 3-[[N$_2$-(benzyloxycarbonyl)-N$_5$-(N-nitroamidino)-L-ornithyl]amino]-p-anisic acid, m.p. 208°-209° C. This is coupled with $\beta$-alanine benzyl ester p-toluenesulphonate in an analogous manner to give the desired ester, m.p. 151°-153° C.

EXAMPLE 4

Analogously to Example 1, from 415 mg of N-[3-[[N$_2$-(benzyloxycarbonyl)-N$_5$-(N-nitroamidino)-L-ornithyl]amino]-p-toluoyl]-$\beta$-alanine benzyl ester there are obtained 264 mg of N-[3-(L-arginylamino)-p-toluoyl]-$\beta$-alanine formate (2:3), $[\alpha]_D^{20} = +18.8°$ (MeOH, c=0.5%).

The ester starting material (m.p. 154°-156° C.) is obtained analogously to Example 3 from N$_\alpha$-Z-N$_\omega$-nitro-L-arginine and 3-amino-4-methylbenzoic acid via m-[[N$_2$-(benzyloxycarbonyl)-N$_5$-(N-nitroamidino)-L-ornithyl]amino]-p-toluic acid, m.p. 235° C. (dec.).

EXAMPLE 5

545 mg of N-[m-[6-[1-benzyloxy)formamido]hexanamido]benzoyl]-$\beta$-alanine benzyl ester and 136 mg of Pd/C are stirred in 10 ml of acetic acid for 3 hours under hydrogen. The filtered solution is evaporated in a vacuum and the residue is dissolved in water and again evaporated. There are obtained 330 mg of N-[m-(6-aminohexanamido)benzoyl]-$\beta$-alanine, m.p. 221° C.

The ester starting material (m.p. 121°-122° C.) is obtained from 6-[1-(benzyloxy)formamido]hexanoic acid and N-(m-aminobenzoyl)-$\beta$-alanine benzyl ester trifluoroacetate analogously to the above Examples.

EXAMPLE 6

Analogously to Example 5, from N-[m-[[N-(benzyloxycarbonyl)-$\beta$-alanyl]amino]benzoyl]-$\beta$-alanine benzyl ester, m.p. 155°-156°, there is obtained N-[m-($\beta$-alanylamino)benzoyl]-$\beta$-alanine, m.p. 238° C.

EXAMPLE 7

Analogously to Example 5, from N-[m-[8-[1-(benzyloxy)formamido]octanamido]benzoyl]-$\beta$-alanine benzyl ester there is obtained N-[m-(8-aminooctanamido)benzoyl]-$\beta$-alanine, m.p. 231°-233° C.

The ester starting material (m.p. 123°-124° C.) is obtained by coupling 8-[1-(benzyloxy)formamidooctanoic acid and 3-aminobenzoic acid to give m-[8-[1-(benzyloxy)formamido]octanamido]benzoic acid, m.p. 167°-168° C., and reacting the latter with $\beta$-alanine benzyl ester p-toluenesulphonate.

EXAMPLE 8

Analogously to the above Examples, from m-[$\alpha$-[1-(benzyloxy)formamido]-p-toluamido]benzoic acid, m.p. 250° C., via N-[m-[$\alpha$-[1-(benzyloxy)formamido]-p-toluamido]benzoyl]-$\beta$-alanine benzyl ester, m.p. 155°-156° C., there is obtained N-[m-($\alpha$-amino-p-toluamido)benzoyl]-$\beta$-alanine, m.p. 232° C.

EXAMPLE 9

Analogously to the above Examples, from m-[5-[1-(benzyloxy)formamido]valeramido]benzoic acid, m.p. 217°-221° C., via N-[m-[5-[1-(benzyloxy)formamido]valeramido]benzoyl]-$\beta$-alanine benzyl ester, m.p.

122°–126° C., there is obtained N-[m-(5-aminovaleramido)benzoyl]-β-alanine, m.p. 192°–194° C.

EXAMPLE 10

439 mg of N-[m-(6-aminohexanamido)benzoyl]-β-alanine (Example 5) and 378 mg of 2-[(aminoiminomethyl)thio]ethanesulphonic acid are stirred at 20° C. for 22 hours in 1.4 ml of saturated sodium carbonate solution. The precipitated N-[m-(6-guanidinohexanamido)benzoyl]-β-alanine is filtered off under suction, washed with water and purified by crystallization, m.p. 248° C.

EXAMPLE 11

Likewise, from N-[m-(8-aminooctanamido)benzoyl]-β-alanine (Example 7) there is manufactured N-[m-(8-guanidinooctanamido)benzoyl]-β-alanine, m.p. 221°–226° C.

EXAMPLE 12

Likewise, from N-[m-(β-alanylamino)benzoyl]-β-alanine (Example 6) there is obtained N-[m-[(N-amidino-β-alanyl)amino]benzoyl]-β-alanine, m.p. 241° C.

EXAMPLE 13

Analogously, from N-[m-(α-amino-p-toluamido)benzoyl]-β-alanine (Example 8) there is manufactured N-[m-(α-guanidino-p-toluamido)benzoyl]-β-alanine, m.p. 221° C.

EXAMPLE 14

750 mg of [m-[Z-Arg(NO$_2$)-NH]-benzoyl]-Asp(OBzl)-Val-OBzl are dissolved in 50 ml of 90% glacial acetic acid and hydrogenated at room temperature in the presence of Pd/C (10%). The hydrogenation has finished after 2 hours. The catalyst is filtered off and the filtrate is lyophilized. There are obtained 490 mg of N-[N-[m-(L-arginylamino)benzoyl]-L-α-aspartyl]-L-valine acetate (1:1), MS: 508 (M+H)+.

The benzyl ester starting material can be prepared as follows:

a) A solution of 7.07 g of Z—Arg(NO$_2$)—OH in 50 ml of DMF is treated at −5° C. while stirring with 2.2 ml of N-methylmorpholine, 2.61 ml of isobutyl chloroformate and then with a solution of 2.74 g of 3-aminobenzoic acid and 2.2 ml of N-methylmorpholine in 40 ml of DMF. The reaction mixture is stirred at −5° C. for 30 minutes and at room temperature for 2 hours; subsequently partitioned between ethyl acetate and 5% KHSO$_4$/10% K$_2$SO$_4$ solution; the organic phase is washed with saturated NaCl solution and dried over Na$_2$SO$_4$. The filtrate is concentrated, the white crystals are filtered off under suction and dried in a vacuum. There are obtained 3.0 g of m-[[N$_2$-(benzyloxycarbonyl)-N$_5$-(N$_1$-nitroamidino)-L-ornithyl]amino]benzoic acid, m.p. 232° C.; [α]$_D^{20}$=+5.9° (c=1, DMF).

b) A solution of 1.42 g of the acid obtained in a) in 15 ml of DMF is treated in succession at −5° C. with 0.33 ml of N-methylmorpholine and 0.39 ml of isobutyl chloroformate and then at −10° C. with a solution of 1.58 g of H-Asp(OBzl)-Val-OBzl.CF$_3$COOH and 0.33 ml of N-methylmorpholine in 10 ml of DMF. The reaction mixture is stirred at −5° C. for 10 minutes and at room temperature for 2 hours and subsequently partitioned between ethyl acetate and water. The organic phase is washed with 5% KHSO$_4$/10% K$_2$SO$_4$ solution, water, saturated NaHCO$_3$ solution, water and saturated NaCl solution and dried over Na$_2$SO$_4$. The drying agent is filtered off and the filtrate is concentrated in a vacuum. The residue is crystallized from ether. There are obtained 1.6 g of [m-[Z-Arg(NO2)-NH]-benzoyl]-Asp(OBzl)-Val-OBzl, m.p. 80° C.; [α]$_D^{20}$=−15.3° (c=1, DMF).

EXAMPLE 15

A solution of 142 mg of N-[N-[m-(L-arginylamino)benzoyl]-L-α-aspartyl]-L-valine acetate (Example 1) in 1 ml of dioxan and 1 ml of H$_2$O is treated in succession with 40 mg of pyridine.HBr, 105 mg of NaHCO$_3$ and 76 mg of di-t-butyl dicarbonate. After shaking at room temperature for 3 hours the reaction mixture is acidified to pH 4 with glacial acetic acid and purified over Sephadex G-25S, a polysaccharide resin, in 0.2N acetic acid. The main fraction is lyophilized and purified by means of HPLC over Lichrosorb RP18, a chemically modified silica gel, with 0.05M ammonium acetate and ethanol. The main fraction is lyophilized from water. There are obtained 54 mg of [m-(Boc-Arg-NH)benzoyl]-Asp-Val, MS: 608 (M+H)+.

EXAMPLE 16

807 mg of N-[3-[6-(1-t-butoxyformamido)hexanamido]-5-nitrobenzoyl]-β-alanine are left to stand at room temperature in 2.7 ml of formic acid for 18 hours. The solvent is evaporated in a vacuum. The residue is dissolved in water and the solution is evaporated in a vacuum. There are obtained 573 mg of N-[3-(6-aminohexanamido)-5-nitrobenzoyl]-β-alanine formate (2:1), MS: 367 (67, M+H).

For the preparation of the starting material, MS: 367 (M-BOC+H), 6-(1-t-butoxyformamido)hexanoic acid and 3-amino-5-nitrobenzoic acid are reacted to give 3-[6-(1-t-butoxyformamido)hexanamido]-5-nitrobenzoic acid, MS: 396 (2, M+H), and the latter is reacted with β-alanine methyl ester to give N-[3-[6-(1-t-butoxyformamido)hexanamido]-5-nitrobenzoyl]-β-alanine methyl ester, MS: 381 (100, M-Boc+H). This is then saponified in methanolic sodium hydroxide solution.

EXAMPLE 17

Analogously to Example 16, from N-[5-[6-(1-t-butoxyformamido)hexanamido]-2-chlorobenzoyl-β-alanine there is obtained N-[5-(6-aminohexanamido)-2-chlorobenzoyl]-β-alanine, m.p. 264° C. from H$_2$O.

For the preparation of the starting material [MS: 456 (1, M+H)], 6-(1-t-butyoxyformamido)hexanoic acid and 5-amino-2-chlorobenzoic acid are coupled to give 5-[6-(1-t-butoxyformamido)hexanamido]-2-chlorobenzoic acid, MS: 385 (2, M+H), the latter is coupled with β-alanine methyl ester to give N-[5-[6-(1-t-butoxyformamido)hexanamido]-2-chlorobenzoyl-β-alanine methyl ester, MS: 470 (14, M+H), and this is then saponified in methanolic sodium hydroxide solution.

EXAMPLE 18

Analogously to Example 16, from N-[5-[3-(1-t-butoxyformamido)propionamido]-2-nitrobenzoyl]-β-alanine t-butyl ester there is obtained N-[5-(β-alanylamino)-2-nitrobenzoyl]-β-alanine, MS: 325 (77, M+H).

For the preparation of the ester starting material, N-(t-butoxycarbonyl)-β-alanine and 5-amino-2-nitrobenzoic acid are coupled to give 5-[3-(1-t-butoxyformamido)propionamido]-2-nitrobenzoic acid, MS: 354 (17, M+H), and the latter is reacted with β-alanine t-butyl ester.

EXAMPLE 19

Analogously to Example 16, from N-[3-[6-[2,3-bis(t-butoxycarbonyl)guanidino]hexanamido]-5-nitrobenzoyl]-β-alanine there is manufactured N-[3-(6-guanidinohexamido)-5-nitrobenzoyl]-β-alanine, MS: 409 (100, M+H).

For the preparation of the starting material, MS: 509 (2, M-Boc+H), N-[3-(6-aminohexanamido)-5-nitrobenzoyl]-β-alanine (Example 16) is reacted with N,N'-bis(t-butoxycarbonyl)-S-methylisothiourea in t-butanol, water and triethylamine at 60° C.

EXAMPLE 20

Analogously to Example 16, from N-[5-[6-[2,3-bis(t-butoxycarbonyl)guanidino]hexanamido]-2-chlorobenzoyl]-β-alanine there is obtained N-[5-(6-guanidinohexanamido)-2-chlorobenzoyl]-β-alanine, m.p. 235° C.

The starting material, MS: 598 (3, M+H), is obtained from N-[5-(6-aminohexanamido)-2-chlorobenzoyl]-β-alanine (Example 17) and N,N'-bis(t-butoxycarbonyl)-S-methylisothiourea.

EXAMPLE 21

1.43 g of N-[m-[7-(1-t-butoxyformamido)heptanamido]benzoyl]-β-alanine benzyl ester and 476 mg of Pd/C are stirred in 28 ml of formic acid for 5 hours under hydrogen. The reaction mixture is filtered and the filtrate is evaporated in a vacuum. The residue is taken up in water and evaporated. 464 mg of N-[m-(7-aminoheptanamido)benzoyl]-β-alanine, m.p. 236° C., are obtained from methanol.

The starting material, m.p. 128°-129° C. (ethyl acetate), is obtained from 7-(1-t-butoxyformamido)heptanoic acid and N-(m-aminobenzoyl)-β-alanine benzyl ester trifluoroacetate.

EXAMPLE 22

Analogously to Example 10, from N-[m-(5-aminovaleramido)benzoyl]-β-alanine (Example 9) there is obtained N-[m-(5-guanidinovaleramido)benzoyl]-β-alanine, m.p. 167°-173° C.

EXAMPLE 23

Likewise, from N-[m-(7-aminoheptanamido)benzoyl]-β-alanine (Example 21) there is obtained N-[m-(7-guanidinoheptanamido)benzoyl]-β-alanine, m.p. 237° C.

EXAMPLE 24

Likewise, from N-[m-(4-aminobutyramido)benzoyl]-β-alanine (Example 25) there is obtained N-[m-(4-guanidinobutyramido)benzoyl]-β-alanine, m.p. >260° C.

EXAMPLE 25

Analogously to Example 5, from N-[m-[4-[1-(benzyloxy)formamido]butyramido]benzoyl]-β-alanine benzyl ester there is obtained N-[m-(4-aminobutyramido)benzoyl]-β-alanine, m.p. 205°-206° C.

For the preparation of the ester starting material, m.p. 119°-120° C. (from ethanol), 4-[1-(benzyloxy)formamido]butyric acid is reacted with m-aminobenzoic acid to give m-[4-[1-(benzyloxy)formamido]butyramidobenzoic acid and the latter is reacted with β-alanine benzyl ester.

EXAMPLE 26

Likewise, from N-[m-[α-[1-(benzyloxy)formamido]-m-toluamido]benzoyl]-β-alanine benzyl ester there is obtained N-[m-(α-amino-m-toluamido)benzoyl]-β-alanine, m.p. 242° C. (from water).

The ester starting material, m.p. 151°-152° C. (from ethanol), is prepared from α-(1-(benzyloxy)formamido]-m-toluic acid and N-(m-aminobenzoyl)-β-alanine benzyl ester trifluoroacetate.

EXAMPLE 27

Likewise, from N-[m-[[N-[(benzyloxy)carbonyl]-3-[p-[N-(benzyloxycarbonyl)amidino]phenyl]-DL-alanyl]amino]benzoyl]-β-alanine benzyl ester there is manufactured N-[m-[[3-(p-amidinophenyl)-DL-alanyl]amino]benzoyl]-β-alanine acetate (1:1), MS: 398 (72, M+H).

For the preparation of the ester starting material, MS: 756 (15, M+H), N-(benzyloxycarbonyl)-3-(p-cyanophenyl)-DL-alanine and N-(m-aminobenzoyl)-β-alanine benzyl ester trifluoroacetate are coupled to give N-[m-[[N-(benzyloxycarbonyl)-3-(p-cyanophenyl)-DL-alanyl]amino]benzoyl]-β-alanine benzyl ester, MS: 605 (15, M+H), and this is converted with hydrogen sulphide and triethylamine in pyridine into N-[m-[[N-(benzyloxycarbonyl)-3-[p-(thiocarbamoyl)phenyl]-DL-alanyl]amino]benzoyl]-β-alanine benzyl ester, m.p. 145°-146° C. (from ethyl acetate). The latter is then reacted with methyl iodide in acetone and subsequently with ammonium acetate in methanol and treated with benzyl chloroformate and triethylamine in THF.

EXAMPLE 28

500 mg of N-[m-[[$N_5$-(benzyloxycarbonyl)-$N_2$-t-butoxycarbonyl-L-ornithyl]amino]benzoyl]-β-alanine benzyl ester, 10 ml of ethanol, 0.05 ml of acetic acid and 125 mg of Pd/C are stirred under hydrogen for 3.5 hours. The reaction mixture is filtered and the filtrate is evaporated in a vacuum. There are obtained 333 mg of N-[m-[[(S)-$N_2$-(t-butoxycarbonyl)-L-ornithyl]amino]benzoyl]-β-alanine acetate (1:1), $[α]_D = -18.1°$ (MeOH, c=0.44%).

The ester starting material, $[α]_D = -13.2°$ (MeOH, c=0.5%), is prepared from $N_2$-(t-butoxycarbonyl)-$N_5$-(benzyloxycarbonyl)-L-ornithine and N-(m-aminobenzoyl)-β-alanine benzyl ester trifluoroacetate.

EXAMPLE 29

512 mg of N-[m-(α-amino-m-toluamido)benzoyl]-β-alanine (Example 26) and 553 mg of 2-[(aminoiminomethyl)thio]ethanesulphonic acid are stirred at 20° C. for 4 days in 3 ml of $H_2O$ and 3 ml of 1N sodium hydroxide solution. The precipitate is centrifuged off, stirred for 20 hours in 5 ml of 0.1N sodium hydroxide solution, centrifuged off and washed with methanol-water 1:1, methanol and ether. There are obtained 512 mg of N-[m-(α-guanidino-m-toluamido)benzoyl]-β-alanine, m.p. 314° C. (dec.).

EXAMPLE 30

Analogously to Example 16, from N-[m-[[(S)-$N_2$-(t-butoxycarbonyl)-L-ornithyl]amino]benzoyl]-β-alanine acetate (1:1) (Example 28) there is obtained N-[m-(L-ornithylamino)benzoyl]-β-alanine formate (1:1), $[α]_D = +40.4°$ (water, c=0.5%).

EXAMPLE 31

293 mg of N-[5-[[N-(t-butoxycarbonyl)-β-alanyl-]amino]anthraniloyl]-β-alanine t-butyl ester are stirred at 20° C. for 3 hours in 1.3 ml of trifluoroacetic acid. The solvent is evaporated in a vacuum, the residue is dissolved in water and evaporated in a vacuum. There are obtained 324 mg of N-[5-(β-alanylamino)anthraniloyl]-β-alanine trifluoroacetate (1:2), MS: 295 (100, M+H).

For the preparation of the ester starting material, MS: 468 (18, M+NH4), 451 (100, M+H), N-(t-butoxycarbonyl)-β-alanine and 5-amino-2-nitrobenzoic acid are reacted to give 5-[3-(1-t-butoxyformamido)propionamido]-2-nitrobenzoic acid, MS: 354 (17, M+H), the latter is reacted with β-alanine t-butyl ester to give N-[5-[3-(1-t-butoxyformamido)propionamido]-2-nitrobenzoyl]-β-alanine t-butyl ester and this is hydrogenated on Pd/C in ethanol.

EXAMPLE 32

296 mg of N-[m-[2-(α-azido-p-tolyl)acetamido]benzoyl]-β-alanine benzyl ester and 74 mg of Pd/C are stirred in 6 ml of acetic acid for 7 hours under hydrogen. After the addition of 3 ml of water the mixture is filtered and the filtrate is evaporated in a vacuum. The residue is taken up in water and the suspension is evaporated in a vacuum. The residue is triturated in methanol, filtered off under suction and dried. There are obtained 125 mg of N-[m-[2-(α-amino-p-tolyl)acetamido]benzoyl]-β-alanine (3:4 hydrate), m.p. 226° C.

The ester starting material, m.p. 108°-109° C. (from ethanol), is prepared from (α-azido-p-tolyl)acetic acid and N-(m-aminobenzoyl)-β-alanine benzyl ester trifluoroacetate.

EXAMPLE 33

A) A solution of 55 mg of N-[N-[m-[[3-(p-amidinophenyl)-N-(t-butoxycarbonyl)-DL-alanyl]amino]benzoyl]-3-(t-butoxycarbonyl)-L-alanyl]-3-(1-naphthyl)-L-alanine (1:1 epimer) in a mixture of 10 ml of methylene chloride and 5 ml of trifluoroacetic acid is held at room temperature for 2 hours while gassing with argon. After evaporation of the solvent there is obtained N-[N-[m-[[3-(p-amidinophenyl)-DL-alanyl]amino]benzoyl]-L-α-aspartyl]-3-(1-naphthyl)-L-alanine trifluoroacetate (1:2), m.p. 165° C. (dec.) (ethanol/ethyl acetate), yield: 84% of theory, MS: 639 (M+H)+.

B) The starting material can be prepared in the following manner:

a) A solution, cooled to 0° C., of 1.95 g of N-Z-aminobenzoic acid is brought to pH 8 by the dropwise addition of N-methylmorpholine while stirring and 2 g of O-benzotriazolyl-N,N,N,N-tetramethyluronium hexafluorophosphate (HBTU) and a solution of 2.1 g of H-Asp(OtBu)-OMe in 160 ml of DMF are added thereto. The mixture is stirred at 0° C. for 1 hour while gassing with argon and kept in a refrigerator overnight. The residue remaining after evaporation of the solvent is taken up in ethyl acetate and the organic phase is washed with saturated sodium bicarbonate solution, water, 10% potassium hydrogen sulphonate solution and water, dried over sodium sulphate, filtered and evaporated. There is obtained 4-t-butyl 1-methyl N-[m-[1-(benzyloxy)formamido]benzoyl]-L-aspartate, m.p. 115°-116° C. (ether/hexane), yield 88% of theory, MS: 457 (M+H)+.

b) 70 ml of 1N NaOH are added dropwise while stirring to a solution of 27.0 g of the product of a) in 200 ml of acetone while cooling with ice and the stirring is continued at this temperature for 2 hours. The pH is adjusted to 4 by the addition of 10% aqueous citric acid and the solvent is removed. By crystallization and subsequent extraction with ether there is obtained, after recrystallization from methylene chloride/hexane, 4-t-butyl 1-hydrogen N-[m-[1-benzyloxy)formamido]benzoyl]-L-aspartate, m.p. 140°-142° C., yield: 89% of theory, MS: 443 (M+H)+.

c) In an analogous manner as described under a), by coupling the product of b) with methyl (S)-α-amino-1-naphthalenepropionate there is obtained N-[N-[m-[1-(benzyloxy)formamido]benzoyl]-3-(t-butoxycarbonyl)-L-alanyl]-3-(1-naphthyl)-L-alanine methyl ester, m.p. 95°-98° C. (ethyl acetate/hexane), yield: 63% of theory, MS: 654 (M+H)+.

d) A solution of 1.9 g of the product of c) in 100 ml of methanol is hydrogenated in the presence of 0.1 g of Pd/C 10%. After the theoretical amount of hydrogen has been taken up the mixture is filtered and the filtrate is evaporated to dryness. Purification by chromatography on silica gel with methylene chloride/MeOH (98:2) gives N-[N-(m-aminobenzoyl)-3-(t-butoxycarbonyl)-L-alanyl]-3-(1-naphthyl)-L-alanine methyl ester, m.p. 70°-72° C. (hexane), yield: 84% of theory, MS: 520 (M+H)+.

e) 67 mg of N-methylmorpholine and 250 mg of HBTU are added to a solution of 200 mg of N-Boc-3-(p-cyanophenyl)-DL-alanine and 294 mg of the product of d) in 10 ml of DMF while stirring and gassing with argon and the mixture is stored overnight. The oil obtained after evaporation of the solvent is dissolved in ethyl acetate, the solution is washed with 5% aqueous sodium bicarbonate solution and water, dried over MgSO4 and evaporated, and the residual foam is purified by chromatography on silica gel with ethyl acetate. There is obtained N-[3-(t-butoxycarbonyl)-N-[m-[[N-(t-butoxycarbonyl)-3-(p-cyanophenyl)-DL-alanyl]amino]benzoyl]-L-alanyl]-3-(1-naphthyl)-L-alanine methyl ester (1:1 epimers), m.p. 182°-185° C. (ethyl acetate/hexane), yield: 39% of theory, MS: 792 (M+H)+.

f) 362 mg of the product of e) are dissolved in 40 ml of pyridine and 3 ml of triethylamine. After saturation with H2S the mixture is stored for 2 days, stirred into water and extracted with ethyl acetate. The crude product is purified by chromatography on silica gel with methylene chloride/methanol (97:3). There is obtained N-[3-(t-butoxycarbonyl)-N-[m-[[N-(t-butoxycarbonyl)-3-[p-(thiocarbamoyl)phenyl]-DL-alanyl]amino]benzoyl]-L-alanyl]-3-(1-naphthyl)-L-alanine methyl ester (1:1 epimers), m.p. 131° C. (dec.), yield: 58% of theory, MS: 826 (M+H)+.

g) The thioamide of f) is dissolved in 30 ml of acetone, treated with 0.6 ml of methyl iodide and heated under reflux for 3 hours. After filtration and concentration the product is precipitated by the addition of ether. There is obtained N-[3-(t-butoxycarbonyl)-N-[m-[[N-(t-butoxycarbonyl)-3-[p-[(methylthio)formimidoyl]phenyl]-DL-alanyl]amino]benzoyl]-L-alanyl]-3-(1-naphthyl)-L-alanine methyl ester hydroiodide (1:1 epimers), m.p. 162°-163° C. (ether), yield: 75% of theory, MS: 840 (M+H)+.

h) A solution of 180 mg of methyl thioimidate hydroiodide of f) in 30 ml of MeOH is treated with 36 mg of ammonium acetate and heated to 60° C. for 5 hours. After cooling and filtration the crude product is precipitated with ether. There is obtained N-[N-[m-[[3-(p-amidinophenyl)-N-(t-butoxycarbonyl)-DL-alanyl-]amino]benzoyl]-3-(t-butoxycarbonyl)-L-alanyl]-3-(1-naphthyl)-L-alanine methyl ester hydroiodide (1:1 epimers), m.p. 170°–171° C. (dec.) (ether), yield: 71% of theory, MS: 809 (M+H)+.

i) Analogously to paragraph b), by the alkaline saponification of the product of h) there is obtained N-[N-[m-[[3-(p-amidinophenyl)-N-(t-butoxycarbonyl)-DL-alanyl]amino]benzoyl]-3-(t-butoxycarbonyl)-L-alanyl]-3-(1-naphthyl)-L-alanine (1:1 epimers), m.p. 263°–265° C. (water), yield: 94% of theory, MS: 795 (M+H)+.

EXAMPLE 34

Analogously to Example 33, by the acidolysis of N-[N-[m-(p-amidinobenzamido)benzoyl]-3-(t-butoxycarbonyl)-L-alanyl]-3-(1-naphthyl)-L-alanine there is obtained N-[N-[m-(p-amidinobenzamido)benzoyl]-L-$\alpha$-aspartyl]-3-(1-naphthyl)-L-alanine trifluoroacetate (1:1.9), m.p. 130° C. (dec.) (hexane), yield: 54% of theory, MS: 596 (M+H)+.

The starting material can be prepared as follows:

a) By coupling 4-cyanobenzoic acid with N-[N-(m-aminobenzoyl)-3-(t-butoxycarbonyl)-L-alanyl]-3-(1-naphthyl)-L-alanine methyl ester there is obtained N-[3-(t-butoxycarbonyl)-N-[m-(p-cyanobenzamido)benzoyl]-L-alanyl]-3-(1-naphthyl)-L-alanine methyl ester, yield: 56% of theory, MS: 649 (M+H)+.

b) By thionation, methylation and ammonolysis of the product of a) there is obtained N-[N-[m-(p-amidinobenzamido)benzoyl]-3-(t-butoxycarbonyl)-L-alanyl]-3-(1-naphthyl)-L-alanine methyl ester hydroiodide, m.p. 87° C. (dec.) (hexane), yield: 74% of theory, MS: 666 (M+H)+.

c) By alkaline saponification of the previous step there is obtained N-[N-[m-(p-amidinobenzamido)benzoyl]-3-(t-butoxycarbonyl)-L-alanyl]-3-(1-naphthyl)-L-alanine, m.p. 230° C. (dec.), yield: 34% of theory, MS: 652 (M+H)+.

EXAMPLE 35

Analogously to Example 32, from 579 mg of N-[m-[p-[N-(benzyloxycarbonyl)amidino]benzamido]benzoyl]-$\beta$-alanine benzyl ester there are obtained 268 mg of N-[m-(p-amidinobenzamido)-benzoyl]-$\beta$-alanine, m.p. 276° C. (dec.).

For the preparation of the ester starting material (m.p. 192° C.), p-amidinobenzoyl chloride hydrochloride, m-aminobenzoyl-$\beta$-alanine benzyl ester trifluoroacetate and triethylamine are reacted at 0°–5° C. for 20 hours in THF. Subsequently, the mixture is treated with benzyl chloroformate and triethylamine and reacted at 0°–5° C. for 30 hours.

EXAMPLE 36

Analogously to Example 1, from N-[m-[[N-[N,N'-bis(t-butoxycarbonyl)amidino]glycyl]amino]benzoyl]-$\beta$-alanine benzyl ester there is obtained N-[m-[(N-amidinoglycyl)amino]benzoyl]-$\beta$-alanine formate (2:1), MS: 308 (33, M+H).

The ester starting material [MS: 598 (4, M+H)] is obtained from glycine and N,N'-bis(t-butoxycarbonyl)-S-methylisothiourea via N-[N,N'-bis(t-butoxycarbonyl)amidino]glycine and N-(m-aminbenzoyl)-$\beta$-alanine benzyl ester trifluoroacetate.

EXAMPLE 37

Analogously to Example 1, from N-[m-[N$_6$-[(benzyloxy)carbonyl]-N$_2$-(t-butoxycarbonyl)-L-lysyl]benzoyl]-$\beta$-alanine benzyl ester there is obtained N-[m-(L-lysylamino)benzoyl]-$\beta$-alanine formate (2:3), MS: 337 (7, M+H).

The starting material [MS: 661 (7, M+H)] is obtained from N$_6$-(benzyloxycarbonyl)-N$_2$-(t-butoxycarbonyl)-L-lysine hydroxysuccinimide ester and N-(m-aminobenzoyl)-$\beta$-alanine benzyl ester in boiling THF.

EXAMPLE 38

Analogously to Example 1, from DL-N-[m-[5-(1-t-butoxyformamido)valeramido]benzoyl]-3-phenyl-$\beta$-alanine benzyl ester there is obtained DL-N-[m-(5-aminovaleramido)benzoyl]-3-phenyl-$\beta$-alanine formate (2:1), MS: 384 (100, M+H).

The starting material can be prepared as follows:

a) DL-3-Amino-3-phenylpropionic acid is esterified with benzyl alcohol and p-toluenesulphonic acid to give DL-3-amino-3-phenylpropionic acid benzyl ester p-toluenesulphonate, MS: 164 (23, M—C$_7$H$_7$).

b) 5-[1-(t-Butoxy)formamido]valeric acid is coupled with m-aminobenzoic acid to give m-[5-(1-t-butoxyformamido)valeramido]benzoic acid, m.p. 188° C., and the latter is reacted with 3-amino-3-phenylpropionic acid benzyl ester p-toluenesulphonate to give DL-N-[m-[5-(1-t-butoxyformamido)valeramido]benzoyl]-3-phenyl-$\beta$-alanine benzyl ester, MS: 574 (17, M+H).

EXAMPLE 39

Analogously to Example 1, from N-[3-[5-(1-t-butoxyformamido)valeramido]-4-chlorobenzoyl]-$\beta$-alanine t-butyl ester there is obtained N-[3-(5-aminovaleramido)-4-chlorobenzoyl]-$\beta$-alanine formate (2:1), m.p. 184°–186° C.

For the preparation of the starting material, 5-[1-(t-butoxy)formamido]valeric acid and 3-amino-4-chlorobenzoic acid are coupled to give 3-[5-(1-t-butoxyformamido)valeramido]-4-chlorobenzoic acid, m.p. 203° C., and the latter is coupled with $\beta$-alanine t-butyl ester to give N-[3-[5-(1-t-butoxyformamido)valeramido]-4-chlorobenzoyl]-$\beta$-alanine t-butyl ester, MS: 498 (60, M+H).

EXAMPLE 40

Analogously to Example 1, from N-[3-[5-(1-t-butoxyformamido)valeramido]-p-toluoyl]-$\beta$-alanine benzyl ester there is obtained N-[3-(4-aminovaleramido)-p-toluoyl]-$\beta$-alanine, m.p. 212°–213° C., as a hydrate (2:1).

For the preparation of the starting material, 5-[1-(t-butoxy)formamido]valeric acid and 3-amino-p-toluic acid are coupled to give 3-[5-(1-t-butoxyformamido)valeramido]-p-toluic acid, m.p. 212° C., and the latter is coupled with $\beta$-alanine benzyl ester to give N-[3-[5-(1-t-butoxyformamido)valeramido]-p-toluoyl]-$\beta$-alanine benzyl ester, m.p. 112°–113° C.

EXAMPLE 41

Analogously to Example 1, from DL-N-[m-[5-(1-t-butoxyformamido)valeramido]benzoyl]-3-(5-indanyl)-$\beta$-alanine there is obtained DL-N-[m-(5-aminovaleramido)benzoyl]-3-(5-indanyl)-$\beta$-alanine trifluoroacetate (2:3), MS: 424 (36, M+H).

The starting material, MS: 524 (87, M+H), is obtained from m-[5-(1-t-butoxyformamido)valeramido]benzoic acid and $\beta$-amino-5-indanepropionic acid.

EXAMPLE 42

Analogously to Example 5, from N-[m-[trans-4-[[1-(benzyloxy)formamido]methyl]cyclohexanecarboxamido]benzoyl]-β-alanine benzyl ester there is obtained N-[m-[trans-4-(aminomethyl)cyclohexanecarboxamido]benzoyl]-β-alanine, m.p. 248°–249° C.

The starting material, m.p. 145°–146° C., is obtained by coupling trans-4-[[1-(benzyloxy)formamido]methyl]-cyclohexanecarboxylic acid with N-(m-aminobenzoyl)-β-alanine benzyl ester.

EXAMPLE 43

Analogously to Example 5, from N-[m-[m-[N-[(benzyloxy)carbonyl]amidino]benzamido]benzoyl]-β-alanine benzyl ester there is obtained N-[m-(m-amidinobenzamido)benzoyl]-β-alanine, m.p. 221°–223° C. (decomposition).

For the preparation of the starting material, m.p. 182°–183° C., 3-cyanobenzoic acid and N-(m-aminobenzoyl)-β-alanine benzyl ester trifluoroacetate are coupled to give N-[m-(m-cyanobenzamido)benzoyl]-β-alanine benzyl ester, MS: 428 (100, M+H), and this is converted with hydrogen sulphide and triethylamine in pyridine into N-[m-[m-(thiocarbamoyl)benzamido]benzoyl]-β-alanine benzyl ester, m.p. 128°–131° C. The latter is then reacted with methyl iodide in acetone and subsequently with ammonium acetate in methanol and treated with benzyl chloroformate and triethylamine in THF.

EXAMPLE 44

Analogously to Example 16, from DL-N-[m-[5-[(E/Z)-2,3-bis(t-butoxycarbonyl)guanidino]valeramido]benzoyl]-3-(5-indanyl)-β-alanine there is obtained DL-N-[m-(5-guanidinovaleramido)benzoyl]-3-(5-indanyl)-β-alanine formate (2:1), MS: 466 (100, M+H).

The starting material is obtained from DL-N-[m-(5-aminovaleramido)benzoyl]-3-(5-indanyl)-β-alanine trifluoroacetate and N,N'-bis(t-butoxycarbonyl)-S-methylisothiourea.

EXAMPLE 45

Analogously to Example 5, from N-[[m-[α-[1-(benzyloxy)formamido]-p-toluamido]phenyl]acetyl]-β-alanine by hydrogenation in acetic acid-methanol 1:1 there is obtained N-[[m-(α-amino-p-toluamido)phenyl]acetyl]-β-alanine, MS: 356 (100, M+H).

The starting material, m.p. 208°–210° C., can be prepared by a) coupling m-nitrophenylacetic acid and β-alanine benzyl ester to give N-[(m-nitrophenyl)acetyl]-β-alanine benzyl ester, MS: 236 (6, M—C$_6$H$_5$—CH$_2$O), b) hydrogenating this to give N-[(m-aminophenyl)acetyl]-β-alanine, MS: 223 (100, M+H), and c) coupling the latter with α-[1-(benzyloxy)formamido]-p-toluic acid.

EXAMPLE 46

Analogously to Example 16, from N-[2-(benzyloxy)-5-[5-(1-t-butoxyformamido)valeramido]benzoyl]-β-alanine there is obtained in 2 hours N-[5-(5-aminovaleramido)-2-(benzyloxy)benzoyl]-β-alanine, m.p. 227°–228° C.

The starting material can be prepared as follows:

a) 5-[1-(t-Butoxy)formamido]valeric acid is coupled with 5-aminosalicyclic acid to give 5-[5-(1-t-butoxyformamido)valeramido]salicylic acid, m.p. 181° C.

b) Therefrom there is obtained with benzyl bromide and potassium carbonate in DMF t-butyl [4-[[4-(benzyloxy)-3-[(benzyloxy)carbonyl]phenyl]carbamoyl]butyl]carbamate, m.p. 104°–106° C.

c) By saponification with NaOH in t-butanol there is obtained therefrom 2-(benzyloxy)-5-[5-(1-t-butoxyformamido)valeramido]benzoic acid, m.p. 133°–134° C.

d) This is coupled with β-alanine benzyl ester to give N-[2-(benzyloxy)-5-[5-(1-t-butoxyformamido)-valeramido]benzoyl]-β-alanine benzyl ester, m.p. 97°–99° C.

e) The latter is saponified in methanol with NaOH to give N-[2-(benzyloxy)-5-[5-(1-t-butoxyformamido)-valeramido]benzoyl]-β-alanine, MS: 514 (51, M+H).

EXAMPLE 47

Analogously to Example 16, from N-[2-(benzyloxy)-5-[5-[(E/Z)-N,N'-bis(t-butoxycarbonyl)guanidino]-valeramido]benzoyl]-β-alanine there is obtained N-[2-(benzyloxy)-5-(5-guanidinovaleramido)benzoyl]-β-alanine, m.p. 242°–245° C.

The starting material, MS: 656 (32, M+H), is obtained from N-[5-(5-aminovaleramido)-2-(benzyloxy)-benzoyl]-β-alanine (Example 46) and N,N'-bis(t-butoxycarbonyl)-S-methyl-isothiourea.

EXAMPLE 48

Analogously to Example 16, from N-[5-[5-[(E or Z)-2,3-bis(t-butoxycarbonyl)guanidino]valeramido]-salicyloyl]-β-alanine there is obtained N-[5-(5-guanidinovaleramido)salicyloyl]-β-alanine, m.p. >260° C., MS: 366 (100, M+H).

The starting material, m.p. >250° C., MS: 566 (28, M+H), is obtained from N-[2-(benzyloxy)-5-[5-[(E/Z)-N,N'-bis(t-butoxycarbonyl)guanidino]valeramido]benzoyl]-β-alanine in ethanol with hydrogen and Pd/C.

EXAMPLE 49

Analogously to Example 5, from N-[α-[p-[N-[(benzyloxy)carbonyl]amidino]benzamido]-m-toluoyl]-β-alanine benzyl ester there is obtained N-[α-(p-amidinobenzamido)-m-toluoyl]-β-alanine, m.p. 286° C.

The starting material, m.p. 157° C., can be prepared as follows:

a) α-(1-t-Butoxyformamido)-m-toluic acid and β-alanine benzyl ester are coupled to give N-[α-(1-t-butoxyformamido)-m-toluoyl]-β-alanine benzyl ester, MS: 413 (4, M+H).

b) Therefrom there is obtained with trifluoroacetic acid N-[(α-amino)-m-toluoyl]-β-alanine benzyl ester trifluoroacetate.

c) The latter is firstly reacted with p-amidinobenzoyl chloride in methylene chloride in the presence of saturated aqueous sodium hydrogen carbonate solution and subsequently reacted with benzyl chloroformate in the presence of sodium carbonate solution.

EXAMPLE 50

Analogously to Example 1, from N-[α-[p-[N-[(benzyloxy)carbonyl]amidino]benzamido]-p-toluoyl]-β-alanine benzyl ester there is obtained N-[α-(p-amidinobenzamido)-p-toluoyl]-β-alanine, m.p. >300° C., MS: 369 (100, M+H).

The starting material, m.p. 188°–192° C., can be prepared as follows:

a) α-(1-t-Butoxyformamido)-p-toluic acid and β-alanine benzyl ester are coupled to give N-[α-(1-t-butoxyformamido)-p-toluoyl]-β-alanine benzyl ester, m.p. 113°–116° C.

b) Therefrom with trifluoroacetic acid there is obtained N-[(α-amino)-p-toluoyl]-β-alanine benzyl ester trifluoroacetate.

c) The latter is reacted firstly with p-amidino-benzoyl chloride and subsequently with benzyl chloroformate.

EXAMPLE 51

550 mg of N-[p-[p-[N,N,N'-tris(t-butoxycarbonyl)amidino]benzamido]benzoyl]-β-alanine were stirred in 10 ml of trifluoroacetic acid for 1 hour. The solvent was evaporated in a vacuum, the residue was dissolved in water and the solution was again evaporated. The residual solid residue was taken up in water and the suspension was adjusted to pH 8–9 with ammonia. After stirring for a short time the crystalline N-[p-(p-amidinobenzamido)benzoyl]-β-alanine was filtered off under suction, washed with water and dried, m.p. >250° C., MS: 355 (21, M+H).

The starting material can be prepared as follows:

a) Methyl p-amidinobenzoate hydrochloride is reacted with di-t-butyl dicarbonate in methylene chloride and aqueous sodium carbonate solution to give methyl p-(N-(t-butoxycarbonyl)amidino]benzoate, m.p. 157° C.

b) Therefrom with di-t-butyl dicarbonate and p-dimethylaminopyridine in acetonitrile there is obtained methyl p-[(E/Z)-tri(t-butoxycarbonyl)amidino]benzoate, m.p. 70°–73° C.

c) This is saponified with methanolic sodium hydroxide solution to give p-[(E/Z)-tri(t-butoxycarbonyl)amidino]benzoic acid, m.p. 157° C.

d) N-(p-Aminobenzamido)-β-alanine is reacted with benzyl alcohol and p-toluenesulphonic acid to give N-(p-aminobenzamido)-β-alanine benzyl ester, m.p. 96°–97° C.

e) The latter is coupled with p-[(E/Z)-tri(t-butoxycarbonyl)amidino]benzoic acid to give N-[p-[p-[N,N,N'-tris(t-butoxycarbonyl)amidino]benzamido]benzoyl]-β-alanine benzyl ester, m.p. 164°–165° C.

f) By catalytic hydrogenation there is obtained therefrom N-[p-[p-[N,N,N'-tris(t-butoxycarbonyl)amidino]benzamido]benzoyl]-β-alanine, m.p. >160° C. (dec.).

EXAMPLE 52

Analogously to Example 5, from N-[m-[2-[p-[[1-(benzyloxy)formamido]formimidoyl]phenyl]acetamido]benzoyl]-β-alanine benzyl ester there is obtained after 48 hours N-[m-[2-(p-amidinophenyl)acetamido]benzoyl]-β-alanine, m.p. 270° C. (dec.), as a hydrate (1:1).

The starting material, m.p. 167° C., can be prepared as follows:

a) p-Cyanophenylacetic acid and N-(m-aminobenzoyl)-β-alanine benzyl ester trifluoroacetate are coupled to give N-[m-[2-(p-cyanophenyl)acetamido]benzoyl]-β-alanine benzyl ester, m.p. 98°–99° C.

b) This is converted with hydrogen sulphide and triethylamine in pyridine into N-[m-[2-[p-(thiocarbamoyl)phenyl]acetamido]benzoyl]-β-alanine benzyl ester, m.p. 163° C. (dec.).

c) The latter is reacted with methyl iodide in acetone, subsequently with ammonium acetate in methanol and finally with benzyl chloroformate in ethyl acetate and saturated sodium carbonate solution.

EXAMPLE 53

Analogously to Example 5, from N-[m-[3-[1-[(benzyloxy)carbonyl]-4-piperidinyl]propionamido]benzoyl]-β-alanine benzyl ester there is obtained N-[m-[3-(4-piperidinyl)propionamido]benzoyl]-β-alanine, m.p. 163° C. (MeOH), as a solvate with MeOH (4:3).

The starting material, MS: 572 (11, M+H), is obtained by coupling 1-[(benzyloxy)carbonyl]-4-piperidinepropionic acid with N-(m-aminobenzoyl)-β-alanine benzyl ester trifluoroacetate.

EXAMPLE 54

Analogously to Example 16, from N-[2-(benzyloxy)-5-[p-[N-(t-butoxycarbonyl)amidino]benzamido]benzoyl]-β-alanine there is obtained in 4 hours N-[5-(p-amidinobenzamido)-2-(benzyloxy)benzoyl]-β-alanine, m.p. 215°–217° C. (lyophilized), as a hydrate (1:4).

The starting material, m.p. >235° C. (dec.), can be prepared as follows:

a) 5-Aminosalicyclic acid is reacted with di-t-butyl dicarbonate and triethylamine in t-butanol and water to give 5-(1-t-butoxyformamido)salicylic acid, m.p. >270° C., MS: 253 (8, M).

b) Therefrom with benzyl bromide and potassium carbonate in acetone there is obtained benzyl 2-(benzyloxy)-5-(1-t-butoxyformamido)benzoate, m.p. 113°–115° C.

c) This is saponified in methanolic sodium hydroxide solution to give 2-(benzyloxy)-5-(1-t-butoxyformamido)benzoic acid, m.p. 136°–139° C.

d) The latter is coupled with β-alanine methyl ester and there is thus obtained N-[2-(benzyloxy)-5-(1-t-butoxyformamido)benzoyl]-β-alanine methyl ester, m.p. 139°–141° C.

e) In trifluoroacetic acid there is obtained therefrom N-[5-amino-2-(benzyloxy)benzoyl]-β-alanine methyl ester, m.p. 80°–83° C.

f) The latter is reacted with p-amidinobenzoyl chloride and subsequently with di-t-butyl dicarbonate to give N-[2-(benzyloxy)-5-[p-[N-(t-butoxycarbonyl)amidino]benzamido]benzoyl]-β-alanine methyl ester, m.p. >270° C. (dec.). MS: 575 (14, M+H).

g) Saponification of this ester with sodium hydroxide solution in methanol-THF gives the starting material.

EXAMPLE 55

173 mg of N-[4-(benzyloxy)-3-[p-[N-(t-butoxycarbonyl)amidino]benzamido]benzoyl]-β-alanine in 4 ml of formic acid are stirred at 20° C. for 4 hours. The reaction mixture is evaporated in a vacuum, the residue is suspended in water and adjusted to pH 8–9 with ammonia. After stirring for a short time the mixture is suction filtered, the filter residue is washed with water and dried at 50° C. in a vacuum. There are obtained 136 mg of N-[3-(p-amidinobenzamido)-4-(benzyloxy)benzoyl]-β-alanine, m.p. >250° C., MS: 461 (41, M+H), as a hydrate (1:1).

The starting material, m.p. >190° C. (dec.), MS: 561 (29, M+H), can be prepared from 3-amino-4-hydroxybenzoic acid in analogy to the procedure described in Example 54 via the following intermediates:

a) 3-(1-t-Butoxyformamido)-4-hydroxybenzoic acid, m.p. >185° C. (dec.), MS: 197 (40, M-C$_4$H$_8$), b) benzyl 4-(benzyloxy)-3-(1-t-butoxyformamido)benzoate, MS: 433 (3, M), c) 4-(benzyloxy)-3-(1-t-butoxyformamido)benzoic acid, m.p. 200°–201° C., d) N-[4-(benzyloxy)-3-(1-t-butoxyformamido)benzoyl]-β-alanine methyl ester, MS: 429 (58, M+H), e) N-[3-amino-4-(benzyloxy)benzoyl]-β-alanine methyl ester, m.p. 121°-122° C., and f) N-[4-(benzyloxy)-3-[p-[N-(t-butoxycarbonyl)amidino]benzamido]benzoyl]-β-alanine methyl ester, m.p. >260° C. (dec.), MS: 575 (29, M+H).

EXAMPLE 56

Analogously to Example 55, from N-[3-[p-[N-(t-butoxycarbonyl)amidino]benzamido]-4-hydroxybenzoyl]-β-alanine there is obtained N-[3-(p-amidinobenzamido)-4-hydroxybenzoyl]-β-alanine, m.p. 253°-255° C. (dec.).

The starting material is obtained from N-[4-(benzyloxy)-3-[p-[N-(t-butoxycarbonyl)amidino]benzamido]benzoyl]-β-alanine methyl ester by catalytic hydrogenation on Pd/C in ethanol-DMF 2:1 to give N-[3-[p-[N-(t-butoxycarbonyl)amidino]benzamido]-4-hydroxybenzoyl]-β-alanine methyl ester, m.p. >180° C. (dec.), MS: 485 (78, M+H), and saponification of the latter in methanolic sodium hydroxide solution.

EXAMPLE 57

Analogously to Example 55, from N-[5-[p-[N-(t-butoxycarbonyl)amidino]benzamido]salicyloyl]-β-alanine there is obtained N-[5-(p-amidinobenzamido)-salicyloyl]-β-alanine. m.p. >260° C., MS: 371 (8, M+H).

The starting material, m.p. 189°-195° C. (dec.), is obtained from N-[2-(benzyloxy)-5-[p-[N-(t-butoxycarbonyl)amidino]benzamido]benzoyl]-β-alanine methyl ester by catalytic hydrogenation on Pd/C in DMF to give N-[5-[p-[N-(t-butoxycarbonyl)amidino]benzamido]salicyloyl]-β-alanine methyl ester, m.p. 177°-179° C., and saponification of the latter in methanolic sodium hydroxide solution.

EXAMPLE 58

Analogously to Example 31, from N-[m-[3-[1-[(E or Z)-N,N'-bis(t-butoxycarbonyl)amidino]-4-piperidinyl]-propionamido]benzoyl]-β-alanine there is obtained N-[m-[3-(1-amidino-4-piperidinyl)propionamido]benzoyl]-β-alanine trifluoroacetate (2:3), MS: 390 (38, M+H).

The starting material, m.p. >240° C. (dec.), is obtained from N-[m-[3-(4-piperidinyl)propionamido]benzoyl]-β-alanine and N,N'-bis(t-butoxycarbonyl)-S-methyl-isothiourea.

EXAMPLE 59

A solution of 3-(t-butoxycarbonyl)-N-[m-[p-[1-(methylthio)formimidoyl]benzamido]benzoyl]-L-alanine methyl ester hydroiodide in methanol is reacted with ammonium acetate in an analogous manner to that described in Example 33 B) h). There is obtained in 71% yield N-[m-(p-amidinobenzamido)benzoyl]-3-(t-butoxycarbonyl)-L-alanine methyl ester hydroiodide in the form of a colourless solid, m.p. 118°-120° C. (ether/isopropyl ether), MS: 469 (M+1)+.

The starting material can be prepared as follows:

a) 4-Cyanobenzoic acid is activated with 2-chloro-4,6-dimethoxy-1,3,5-triazine and N-methylmorpholine analogously to Example 1 and subsequently reacted with 3-aminobenzoic acid in DMF/CH₂Cl₂. There is obtained m-(p-cyanobenzamido)benzoic acid in the form of colourless crystals. Yield: 70%, m.p. 267° C. (ethyl acetate/acetonitrile).

b) m-(p-Cyanobenzamido)benzoic acid is activated in the same manner as described under a) and coupled with the p-toluenesulphonate of H-Asp(OtBu)OMe in DMF at room temperature. There is isolated 3-(t-butoxycarbonyl)-N-[m-(p-cyanobenzamido)benzoyl]-L-alanine methyl ester in the form of colourless crystals. Yield: 65%, m.p. 83°-84° C. (hexane).

c) The nitrile of b) is treated with H₂S in an analogous manner to that described in Example 33 B) f), whereby 3-(t-butoxycarbonyl)-N-[m-[p-(thiocarbamoyl)benzamido]benzoyl]-L-alanine methyl ester is obtained as a yellow solid. Yield: 93%, m.p. 97°-99° C. (hexane).

d) The reaction of the thioamide of c) with methyl iodide is effected in analogy to Example 33 B) g). There is obtained 3-(t-butoxycarbonyl)-N-[m-[p-[1-(methylthio)formimidoyl]benzamido]benzoyl]-L-alanine methyl ester hydroiodide as a yellow crystallizate. Yield: 90%, m.p. 167°-169° C. (dec., ether), MS: 500 (M+1)+.

EXAMPLE 60

A solution of N-[m-(p-amidinobenzamido)benzoyl]-3-(t-butoxycarbonyl)-L-alanine methyl ester hydroidide in CH₂Cl₂/trifluoroacetic acid is left to stand at room temperature for 3 hours. After removal of the solvent and recrystallization of the residue from ethanol/ether there is obtained (S)-3-[m-(p-amidinobenzamido)benzamido]-3-(methoxycarbonyl)propionic acid trifluoroacetate in the form of a colourless solid. Yield: 75%, m.p. 132°-134° C. (decomposition). MS: 413 (M+H)+.

EXAMPLE 61

A solution of N-[m-(p-amidinobenzamido)benzoyl]-3-(t-butoxycarbonyl)-L-alanine methyl ester hydroiodide in methanol is treated with 1N sodium hydroxide solution. After 3 hours at room temperature the mixture is neutralized with 1N hydrochloric acid. The separated product, N-[m-(p-amidinobenzamido)benzoyl]-3-(t-butoxycarbonyl)-L-alanine, is filtered off under suction and dried in a high vacuum. Yield: 75%, m.p. 218°-220° C. MS: 455 (M+H)+.

EXAMPLE 62

In an analogous manner to Example 60, from N-[m-(p-amidinobenzamido)benzoyl]-3-(t-butoxycarbonyl)-L-alanine there is obtained N-[m-(p-amidinobenzamido)benzoyl]-L-asparagine trifluoroacetate (1:2) as a colourless solid. Yield: 80%, m.p. 107°-108° C. (Et₂O; dec.), MS: 399 (M+1)+.

EXAMPLE 63

The ammonolysis of (S)-3-[m-(p-amidinobenzamido)-benzamido]-3-(methoxycarbonyl)propionic acid in NH₃/CH₃OH gives, after removal of the solvent, (S)-3-[m-(p-amidinobenzamido)benzamido]-3-(aminocarbonyl)propionic acid as a colourless solid. Yield: 50%, m.p. 248°-249° C. (MeOH, dec.).

EXAMPLE 64

The coupling of N-[N-(m-aminobenzoyl)-3-(t-butoxycarbonyl)-L-alanyl]-3-phenyl-L-alanine t-butyl ester with 1-amidino-4-piperidinecarboxylic acid is effected analogously to Example 33 B) a) in the presence of pyridinium hydrochloride. The product obtained after the usual working-up is treated at once with trifluoroacetic acid/CH₂Cl₂, whereby there is obtained, after evaporation of the solvent and recrystallization from methanol/ethyl acetate, N-[N-[m-(1-amidino-4-piperidinecarboxamido)benzoyl]-L-α-aspartyl]-3-phenyl-L-alanine trifluoroacetate in the form of a yellow solid. Yield: 11% (over both steps), m.p. 150° C., MS: 553 (M+H)+.

The starting material can be prepared as follows:

N-[N-(m-Aminobenzoyl)-3-(t-butoxycarbonyl)-L-alanyl]-3-phenyl-L-alanine t-butyl ester, MS: 512 (M+1)+, is obtained by coupling 3-aminobenzoic acid with H-Asp(OtBu)-Phe-OtBu (obtained from the condensation of Z-Asp(OtBu)-OH with H-Phe-OtBu followed by hydrogenolysis) in the manner described in Example 59 a).

EXAMPLE 65

Analogously to Example 60, by the acidolysis of N-[N-[m-[2-(p-amidinophenyl)acetamido]benzoyl]-3-(t-butoxycarbonyl)-L-alanyl]-3-phenyl-L-alanine t-butyl ester hydroiodide (1:1) there is obtained the trifluoroacetate salt of N-[N-[m-[2-(p-amidinophenyl)acetamido]benzoyl]-L-α-aspartyl]-3-phenyl-L-alanine in the form of a beige solid. Yield: 51%, m.p. 160° C. (ethyl acetate/hexane, dec.), MS: 560 (M+1)+.

The starting material can be prepared as follows:

a) Coupling of N-[N-(m-aminobenzoyl)-3-(t-butoxycarbonyl)-L-alanyl]-3-phenyl-L-alanine t-butyl ester (Example 64) with 4-cyanophenylacetic acid analogously to Example 33 B) a) gives N-[3-(t-butoxycarbonyl)-N-[m-[2-(p-cyanophenyl)acetamido]benzoyl]-L-alanyl]-3-phenyl-L-alanine t-butyl ester. Yield: 64%, m.p. 90° C. (ethyl acetate/hexane), MS: 655 (M+1)+.

b) By thionation of the product of a) in accordance with Example 33 B) f) there is obtained N-[3-(t-butoxycarbonyl)-N-[m-[2-[p-(thiocarbamoyl)phenyl]acetamido]benzoyl]-L-alanyl]-3-phenyl-L-alanine t-butyl ester as a yellow crystallizate. Yield: 78%, m.p. 99° C. (ethyl acetate/hexane, dec.), MS: 689 (M+1)+.

c) By methylating the product of b) analogously to Example 33 B) g) there is obtained N-[3-(t-butoxycarbonyl)-N-[m-[2-[p-[1-(methylthio)formimidoyl]phenyl]acetamido]benzoyl]-L-alanyl]-3-phenyl-L-alanine t-butyl ester hydroiodide. Yield: 77%, m.p. 115° C. (ethyl acetate/hexane, dec.), MS: 703 (M+1)+.

d) Ammonolysis of the product of c) analogously to Example 33 B) h) gives N-[N-[m-[2-(p-amidinophenyl)acetamido]benzoyl]-3-(t-butoxycarbonyl)-L-alanyl]-3-phenyl-L-alanine t-butyl ester hydroidide. Yield: 89%, m.p. 125° C. (ethyl acetate/hexane, dec.), MS: 672 (M+1)+.

EXAMPLE A

A compound of formula I can be used in a manner known per se as the active ingredient for the manufacture of tablets of the following composition:

| | Per tablet |
|---|---|
| Active ingredient | 200 mg |
| Microcrystalline cellulose | 155 mg |
| Maize starch | 25 mg |
| Talc | 25 mg |

| | Per tablet |
|---|---|
| Hydroxypropylmethylcellulose | 20 mg |
| | 425 mg |

EXAMPLE B

A compound of formula I can be used in a manner known per se as the active ingredient for the manufacture of capsules of the following composition:

| | Per capsule |
|---|---|
| Active ingredient | 100.0 mg |
| Maize starch | 20.0 mg |
| Lactose | 95.0 mg |
| Talc | 4.5 mg |
| Magnesium stearate | 0.5 mg |
| | 220.0 mg |

We claim:

1. A compound of formula $$R^e-N\diagdown\text{piperidine}\diagup-(CH_2)_{0-2}-CONH-$$

$$-(CH_2)_{0-1}-\text{phenyl}-(CH_2)_{0-1}-CONH-CH(R^3)-CH_2COOH$$

wherein $R^e$ is H or amidino;

$R^2$ is H, $CH_3$, $OCH_3$, $NO_2$, halogen, $NH_2$, $-NHCO-$phenylene$-COOH$, $-NHCO(CH_2)_{1-4}-COOH$, $OR^h$, $-CH_2CH_2OR^h$, $-CH_2CH_2OCH_2CH_2OR^h$ or $-CH_2COOR^h$ wherein $R^h$ is H or lower alkyl;

$R^3$ is H, $-CONH_2$, $-COR^f$, $-COOR^g$ or aryl wherein $R^f$ is the residue of an α-aminocarboxylic acid attached via the amino group or an ester or amide thereof, and $R^g$ is H or lower alkyl.

2. The compound of claim 1 selected from the group consisting of:

N-[N-[m-(1-amidino-4-piperidinecarboxamido)benzoyl]-L-α-aspartyl]-3-phenyl-L-alanine trifluoroacetate, N-[m-[3-(4-piperidinyl)propionamido]benzoyl]-β-alanine and N-[m-[3-(1-amidino-4-piperidinyl)propionamido]benzoyl]-β-alanine trifluoroacetate.

3. A compound of the formula $$R^e-N\diagdown\text{piperidine}\diagup-(CH_2)_{0-2}-CONH-(CH_2)_{0-1}-\text{phenyl}(R^2)-(CH_2)_{0-1}-CONH-CH(R^3)-CH_2COOR^4$$

wherein $R^4$ is hydrogen or a readily cleavable ester group and $R^e$, $R^2$ and $R^3$ are as in claim 1 wherein the molecule contains at least one readily cleavable ester group or a protected amino, amidino or guanidino group.

* * * * *